US005879926A

United States Patent [19]

Lemoine et al.

[11] Patent Number: 5,879,926

[45] Date of Patent: *Mar. 9, 1999

[54] YEAST STRAINS FOR THE PRODUCTION OF MATURE HETEROLOGOUS PROTEINS, ESPECIALLY HIRUDIN

[75] Inventors: Yves Lemoine, Strasbourg; Martine Nguyen, Wittersheim, both of France; Tilman Achstetter, Oberkirch, Germany

[73] Assignee: Transgene S.A., Courbevoie, France

[*] Notice: The term of this patent shall not extend beyond the expiration date of Pat. No. 5,521,093.

[21] Appl. No.: 485,515

[22] Filed: Jun. 7, 1995

Related U.S. Application Data

[62] Division of Ser. No. 393,025, Feb. 23, 1995, Pat. No. 5,521,093, which is a continuation of Ser. No. 191,354, Feb. 2, 1994, abandoned, which is a continuation of Ser. No. 26,121, Mar. 4, 1993, abandoned, which is a continuation of Ser. No. 500,885, Mar. 29, 1990, abandoned.

[30] Foreign Application Priority Data

Mar. 31, 1989 [FR] France .................................. 89 04306

[51] Int. Cl.[6] ............................ C12N 1/19; C12N 15/15; C12N 15/12; C07H 21/04

[52] U.S. Cl. ................................ 435/254.2; 435/254.21; 435/69.1; 435/69.2; 435/69.7; 435/320.1; 536/23.2; 536/23.4; 536/23.5; 536/24.2

[58] Field of Search ................................ 435/69.1, 69.2, 435/69.7, 172.3, 224, 254.21, 320.1; 536/23.2, 23.4, 23.5, 24.2

[56] References Cited

U.S. PATENT DOCUMENTS

| | | | |
|---|---|---|---|
| 5,077,204 | 12/1991 | Brake et al. | 435/68.1 |
| 5,521,093 | 5/1996 | Lemoine et al. | 435/320.1 |

FOREIGN PATENT DOCUMENTS

| | | |
|---|---|---|
| 0206783 | 12/1986 | European Pat. Off. . |
| 0252854 | 7/1987 | European Pat. Off. . |
| 0273800 | 7/1988 | European Pat. Off. . |
| 0319944 | 6/1989 | European Pat. Off. . |
| 0327797 | 8/1989 | European Pat. Off. . |
| 0341215 | 11/1989 | European Pat. Off. . |
| 0349435 | 1/1990 | European Pat. Off. . |

OTHER PUBLICATIONS

Julius et al., "Isolation of the putative structural gene for the lysine–arginine–cleaving endopeptidase required for processing of yeast prepro–alpha–factor", Cell 37: 1075–1089, Jul. 1984.

D. H. Wolf et al., *Eur. J. Biochem.*, 73:553–556, "Studies on a Carboxypeptidase Y Mutant of Yeast and Evidence for a Second Carboxypeptidase Activity," (1977).

D. H. Wolf et al., *Journal of Bacteriology*, 147:2:418–426, "Carboxypeptidase S– and Carboxypeptidase Y–Deficient Mutants of Saccharomyces cerevisiae," (1981).

E. W. Jones et al., *Chemical Abstracts*, vol. 98, No. 7, p. 363, Abstract No. 50144u.

K. Struhl, *Nucleic Acids Research*, 13:23:8587–8601, "Nucleotide sequence and transcriptional mapping of the yeast pet56–his3–ded1 gene region," (1985).

A. Dmochowska et al., *Cell*, 50:573–584, "Yeast KEX1 gene encodes a putative protease with a carboxypeptidase B–like function involved in killer toxin and alpha–factor precursor processing," (1987).

L. A. Valls et al., *Cell*, 48:887–897, "Protein Sorting in Yeast: The Localization Determinant of Yeast Vacuolar Carboxypeptidase Y Resides in the Propeptide," (1987).

Y. Bourbonnais et al., *The Journal of Biological Chemistry*, vol. 263, No. 30, pp. 16342–15347 (1988).

G. Loison et al., *Biotechnology*, 6:72–77, "Expression and secretion in S. Cerevisiae of biologically active leech hirudin," (1988).

D. Sleep et al., *Yeast*, 4:E32 (1988).

K. Steube et al., *Yeast*, 4:E33 (1988).

R. S. Fuller et al., *Journal of Cellular Biochemistry*, supplement 12B, p. 271, "The yeast pro–hormone cleaving enzyme, KEX2," (1988).

*Primary Examiner*—Jasemine C. Chambers
*Assistant Examiner*—Scott D. Priebe
*Attorney, Agent, or Firm*—Burns, Doane, Swecker & Mathis, L.L.P.

[57] ABSTRACT

The present invention relates to an improved system for producing mature heterologous proteins, and especially hirudin, by means of yeasts comprising an expression vector containing a sequence coding for the heterologous protein. This improvement is characterized by amplification of the KEX2 gene of yeast, coding for the endoprotease yscF. The amplification is carried out either by integration of one or more copies of all or part of the KEX2 gene in the yeast genome, or by insertion of one or more copies of all or part of the KEX2 gene into the vector for expression of the heterologous protein.

14 Claims, 8 Drawing Sheets

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| HV1 | VAL | VAL | TYR | THR | ASP | CYS | THR | GLU | SER | GLY | GLN | ASN | LEU | CYS | LEU |
| MV2 | ILE | THR | TYR | THR | ASP | CYS | THR | GLU | SER | GLY | GLN | ASN | LEU | CYS | LEU |
| HY3 | ILE | TRH | TYR | THR | ASP | CYS | THR | GLU | SER | GLY | GLN | ASN | LEU | CYS | LEU |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| CYS | GLU | GLY | SER | ASN | YAL | CYS | GLY | GLN | GLY | ASN | LYS | CYS | ILE | LEU |
| CYS | GLU | GLY | SER | ASN | YAL | CYS | GLY | LYS | GLY | ASN | LYS | CYS | ILE | LEU |
| CYS | GLU | GLY | SER | ASN | VAL | CYS | GLY | LYS | GLY | ASN | LYS | CYS | ILE | LEU |

| 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| GLY | SER | ASP | GLY | GLU | LYS | ASN | GLN | CYS | VAL | THR | GLY | GLU | GLY | THR | PRO | LYS |
| GLY | SER | ASN | GLY | LYS | GLY | ASN | GLN | CYS | VAL | THR | GLY | GLU | GLY | THR | PRO | ASN |
| GLY | SER | GLN | GLY | LYS | ASP | ASN | GLN | CYS | VAL | THR | GLY | GLU | GLY | THR | PRO | LYS |

| 48 | 49 | 50 | 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| PRO | GLN | SER | HIS | ASN | ASP | GLY | ASP | PHE | GLU | GLU | ILE | PRO | GLU | GLN | TYR | LEU | CLN |
| PRO | GLU | SER | HIS | ASN | ASN | GLY | ASP | PHE | GLU | GLU | ILE | PRO | GLU | GLN | TYR | LEU | CLN |
| PRO | GLN | SER | HID | ASN | GLN | GLY | ASP | PHE | GLU | PRO | ILE | PRO | GLU | ASP | TYR | ASP | GLU |
| | | | | | | | | | | | | | | | 64 | 65 | 66 |

ALA
63

FIG.1

```
1         10                  20                  30                  40                  50
.SmaI
CCCGGGAATC TCGGTCGTAA TGATTTTTAT AATGACGAAA AAAAAAAAAT

TGGAAAGAAA AAGCTTTAAT GCGGTAGTTT ATCACAGTTA AATTGCTAAC    -100

GCAGTCAGGC ACCGTGTATG AAATCTAACA ATGCGCTCAT CGTCATCCTC

GGCACCGTCA CCCTGGATGC TGTAGGCATA GGCTTGGTTA TGCCGGTACT    -200

GCCGGGCCTC TTGCGGGATA TCGTCCATTC CGACAGCATC GCCAGTCACT

ATGGCGTGCT GCTAGCGCTA TATGCGTTGA TGCAATTTCT ATGCGCACCC    -300

GTTCTCGGAG CACTGTCCGA CCGCTTTGGC CGCCGCCCAG TCCTGCTCGC
                                  Sau3A
TTCGCTACTT GGAGCCACTA TCGACTACGC GATCATGGCG ACCACACCCG    -400

TCCTGTGGAT CTTGGATATA CTTCAAAGCC GACTATGGTA TTTTTATCAT

TATCACTGGC ATGAAAACGT ATTACCAGCA TTACGTGATT ATGCAGATAG    -500
                                              XhoI
GTTTTATCTG TATCAGGATC AAATCGTTAC CTTCATCCTC GAGCACAACA

ACTGCTACTG CCTCCGCCAA CGATAACGGA GCAACTTCAA ACATCAATGG    -600

ACAAGATCAC TGGCTGCCAC GTCGATGAAA CGTCTAAATT ACCACTTCGC

TACCGCGTTG AAAATTCCTG GGGTAAAGAC TCCGGTAAAG ACGGATTATA    -700

CGTGATGACT CAAAAGTACT TCGAGGAGTA CTGCTTTCAA ATTGTGGTCG

ATATCAATGA ATTGCCAAAA GAGCTGGCTT CAAAATTCAC CTCAGGTAAG    -800

GAAGAGCCGA TTGTCTTGCC CATCTGGGAC CCAATGGGTG CTTTGGCCAA

ATAAATAGTT TCAGCAGCTC TGATGTAGAT ACACGTATCT CGACATGTTT    -900

TATTTTTACT ATACATACAT AAAAGAAATA AAAAATGATA ACGTGTATAT

TATTATTCAT ATAATCAATG AGGGTCATTT TCTGAAACGC AAAAAACGGT    -1000

AAATGGAAAA AAAATAAAGA TAGAAAAAGA AAACAAACAA AGGAAAGGTT

AGCATATTAA ATAACTGAGC TGATACTTCA ACAGCATCGC TGAAGAGAAC    -1100

AGTATTGAAA CCGAAACATT TTCTAAAGGC AAACAAGGTA CTCCATATTT

GCTGGACGTG TTCTTTCTCT CGTTTCATAT GCATAATTCT GTCATAAGCC    -1200

TGTTCTTTTT CCTGGCTTAA ACATCCCGTT TTGTAAAAGA GAAATCTATT
```

FIG. 2A

| 1 | 10 | 20 | 30 | 40 | 50 | |
|---|---|---|---|---|---|---|

CCACATATTT CATTCATTCG GCTACCATAC TAAGGATAAA CTAATCCCGT -1300
TGTTTTTTGG CCTCGTCACA TAATTATAAA CTACTAACCC ATTATCAGAT
start
GAAAGTGAGG AAATATATTA CTTTATGCTT TTGGTGGGCC TTTTCAACAT -1400
CCGCTCTTGT ATCATCACAA CAAATTCCAT TGAAGGACCA TACGTCACGA
CAGTATTTTG CTGTAGAAAG CAATGAAACA TTATCCCGCT TGGAGGAAAT -1500
GCATCCAAAT TGGAAATATG AACATGATGT TCGAGGGCTA CCAAACCATT
ATGTTTTTTC AAAAGAGTTG CTAAAATTGG GCAAAAGATC ATCATTAGAA -1600
GAGTTACAGG GGGATAACAA CGACCACATA TTATCTGTCC ATGATTTATT
CCCGCGTAAC GACCTATTTA AGAGACTACC GGTGCCTGCT CCACCAATGG -1700
ACTCAAGCTT GTTACCGGTA AAAGAAGCTG AGGATAAACT CAGCATAAAT
GATCCGCTTT TTGAGAGGCA GTGGCACTTG GTCAATCCAA GTTTTCCTGG -1800
CAGTGATATA AATGTTCTTG ATCTGTGGTA CAATAATATT ACAGGCGCAG
GGGTCGTGGC TGCCATTGTT GATGATGGCC TTGACTACGA AAATGAAGAC -1900
TTGAAGGATA ATTTTTGCGC TGAAGGTTCT TGGGATTTCA ACGACAATAC
CAATTTACCT AAACCAAGAT TATCTGATGA CTACCATGGT ACGAGATGTG -2000
CAGGTGAAAT AGCTGCCAAA AAAGGTAACA ATTTTTGCGG TGTCGGGGTA
GGTTACAACG CTAAAATCTC AGGCATAAGA ATCTTATCCG GTGATATCAC -2100
TACGGAAGAT GAAGCTGCGT CCTTGATTTA TGGTCTAGAC GTAAACGATA
TATATTCATG CTCATGGGGT CCCGCTGATG ACGGAAGACA TTTACAAGGC -2200
CCTAGTGACC TGGTGAAAAA GGCTTTAGTA AAAGGTGTTA CTGAGGGAAG
AGATTCCAAA GGAGCGATTT ACGTTTTTGC CAGTGGAAAT GGTGGAACTC -2300
GTGGTGATAA TTGCAATTAC GACGGCTATA CTAATTCCAT ATATTCTATT
ACTATTGGGG CTATTGATCA CAAAGATCTA CATCCTCCTT ATTCCGAAGG -2400
TTGTTCCGCC GTCATGGCAG TCACGTATTC TTCAGGTTCA GGCGAATATA
TTCATTCGAG TGATATCAAC GGCAGATGCA GTAATAGCCA CGGTGGAACG -2500
TCTGCGGCTG CTCCATTAGC TGCCGGTGTT TACACTTTGT TACTAGAAGC

FIG.2B

```
1         10         20         30         40         50
.         .          .          .          .          .
CAACCCAAAC CTAACTTGGA GAGACGTACA GTATTTATCA ATCTTGTCTG  -2600
CGGTAGGGTT AGAAAAGAAC GCTGACGGAG ATTGGAGAGA TAGCGCCATG
GGGAAGAAAT ACTCTCATCG CTATGGCTTT GGTAAAATCG ATGCCCATAA  -2700
GTTAATTGAA ATGTCCAAGA CCTGGGAGAA TGTTAACGCA CAAACCTGGT
TTTACCTGCC AACATTGTAT GTTTCCCAGT CCACAAACTC CACGGAAGAG  -2800
ACATTAGAAT CCGTCATAAC CATATCAGAA AAAAGTCTTC AAGATGCTAA
CTTCAAGAGA ATTGAGCACG TCACGGTAAC TGTAGATATT GATACAGAAA  -2900
TTAGGGGAAC TACGACTGTC GATTTAATAT CACCAGCGGG GATAATTTCA
AACCTTGGCG TTGTAAGACC AAGAGATGTT TCATCAGAGG GATTCAAAGA  -3000
CTGGACATTC ATGTCTGTAG CACATTGGGG TGAGAACGGC GTAGGTGATT
GGAAAATCAA GGTTAAGACA ACAGAAAATG GACACAGGAT TGACTTCCAC  -3100
AGTTGGAGGC TGAAGCTCTT TGGGGAATCC ATTGATTCAT CTAAAACAGA
AACTTTCGTC TTTGGAAACG ATAAAGAGGA GGTTGAACCA GCTGCTACAG  -3200
AAAGTACCGT ATCACAATAT TCTGCCAGTT CAACTTCTAT TTCCATCAGC
GCTACTTCTA CATCTTCTAT CTCAATTGGT GTGGAAACGT CGGCCATTCC  -3300
CCAAACGACT ACTGCGAGTA CCGATCCTGA TTCTGATCCA AACACTCCTA
AAAAACTTTC CTCTCCTAGG CAAGCCATGC ATTATTTTTT AACAATATTT  -3400
TTGATTGGCG CCACATTTTT GGTGTTATAC TTCATGTTTT TTATGAAATC
                                              EcoRI
AAGGAGAAGG ATCAGAAGGT CAAGAGCGGA AACGTATGAA TTCGATATCA  -3500
                                           * deletion
TTGATACAGA CTCTGAGTAC GATTCTACTT TGGACAATGG AACTTCCGGA
ATTACTGAGC CCGAAGAGGT TGAGGACTTC GATTTTGATT TGTCCGATGA  -3600
AGACCATCTT GCAAGTTTGT CTTCATCAGA AAACGGTGAT GCTGAACATA
CAATTGATAG TGTACTAACA AACGAAAATC CATTTAGTGA CCCTATAAAG  -3700
CAAAAGTTCC CAAATGACGC CAACGCAGAA TCTGCTTCCA ATAAATTACA
AGAATTACAG CCTGATGTTC CTCCATCTTC CGGACGATCG TGATTCGATA  -3800
          HindIII                 deletion  * stop
TGTACAGAAA GCTTCAAATT ACAAAATAGC ATTTTTTTCT TATAGATTAT
```

FIG. 2C 1 10 20 30 40 50

AATACTCTCT CATACGTATA CGTATATGTG TATATGATAT ATAAACAAAC -3900

ATTAATATCC TATTCCTTCC GTTTGAAATC CCTATGATGT ACTTTGCATT

GTTTGCACCC GCGAATAAAA TGAAAACTCC GAACCGATAT ATCAAGCACA -4000

BamHI

TAAAAGGGGA <u>GGGTCC</u>AATT AATGCATATT TAAGACCACA GCTGAATAAC

TTTAAAACGG CAGACAAAAC AAAAAATAGG TCGAATAAAC CTTACCTGCC -4100

TAGAAGGAAT GACAGCAGCT AATAAGAATA TTGTCTTCGG ATTTTCCAGA

TCCATTAGCG CAATTCTACT AATATGCTTT TTCTTTGAAA AAGTCTGCGG -4200

TGATATGGAG CATGATATGG GCATGGATGA TACTTCGGGA TACACGAGGC

CAGAAATTGT GCAGGCTGGG TCGAAATCTT TCCACTGGCT CTGCACTTTG -4300

GGATTCTTGT TGCTTTTACC ATCCGTGGTG ACGTGCCTTT CGTTCGCTGG

CAGGATATAT TCAGCTACCC TCTTACAATG CACTTGTGCC GTTTACGCTT -4400

TCTTAGAAGC TGCCGTATTA AGATTTCAAG ACAATGATGG GGTAGAAAAT

AGAACTTCAA GGGGAACCGC ATGGTTTTTG GTGGGACTTA CTTGGATAAC -4500

CTTATTCTTT GGTGGATTAG CTGGAGGAAC TGGTTTCTTA GTGAAAAGCA

AGAGGTTGCA AACGTTCATA TCAAATGCAG GTGAGAAAAG GTTGTCATAT -4600

ATCCATCGTG GTTTATCCTT TCTAACTGTT CTAACAGGTT GGGTTAAAGT

CTGTTTGGCA CCTGTTGCGC TCTTTGGGTT TTGTAGAGAG GCACACACAG -4700

GGCAATGCAT CGCTCATGGT ATCATGGGAT CC

FIG. 2D

YEAST STRAINS FOR THE PRODUCTION OF MATURE HETEROLOGOUS PROTEINS, ESPECIALLY HIRUDIN

This application is a divisional of application Ser. No. 08/393,025, filed Feb. 23, 1995 now U.S. Pat. No. 5,521,093, which is a continuation of application Ser. No. 08/191,354 filed Feb. 2, 1994, now abandoned, which is a continuation of application Ser. No. 08/026,121 filed Mar. 4, 1993 (now abandoned), which was a continuation of application Ser. No. 07/500,885 filed Mar. 29, 1990, now abandoned.

The present invention relates to an improvement made to the preparation of heterologous proteins by means of recombinant yeasts, such as *Saccharomyces cerevisiae*, and more especially the preparation of hirudin. It relates, in the first place, to a new yeast strain productive of the heterolgous protein, transformed with a vector permitting expression of the protein in mature form.

Yeasts are unicellular eukaryotic organisms; the yeast genus Saccharomyces comprises strains whose biochemistry and genetics are intensively studied in the laboratory; it also comprises strains used in the food industry (bread, alcoholic drinks, etc.) and consequently produced in very large quantities. The ease with which the genetics of *Saccharomyces cerevisiae* cells may be manipulated and the long industrial history of this species hence make it a host of choice for the production of foreign proteins using recombinant DNA techniques.

When it is desired to obtain proteins of industrial importance, intended for production in large quantities, it is desirable that, in order for it to retain the desired properties, the protein is produced essentially in mature form, that is to say bereft of any additional amino acid or peptide sequence remaining fused to the protein. This is especially desirable in the case of hirudin. In effect, hirudin, the main source of which is in the salivary glands of medicinal leeches in the form of a mixture of peptides of 65 to 66 amino acids, is a very specific and very effective inhibitor of thrombin. It is hence a very advantageous therapeutic agent, whose use in clinical medicine demands very high purity of an active product.

A number of natural variants of hirudin have been identified and designated HV1, HV2 and HV3. Their structure is shown in FIG. 1. Subsequently, these natural variants, as well as other analogues, have been prepared by genetic engineering, especially by fermentation of *S. cerevisiae* strains, as described, for example, in European Patent Publications EP-A-0,252,854 and EP-A-0,273,800 in the name of the Applicant.

As has already been stated, *S. cerevisiae* yeast is hence especially advantageous for the production of heterologous proteins, that is to say proteins which are neither produced naturally by the yeast nor necessary to its growth. In effect, this yeast is itself capable of secreting some proteins into the culture medium, correctly processed, that is to say in a mature form. For example, the alpha sex pheromone is found in the culture medium of an alpha mating type strain of *Saccharomyces cerevisiae*.

The alpha sex pheromone of yeast is a peptide of 13 amino acids. Kurjan and Herskowitz (1982, Cell. 30, 933–934) cloned the structural gene for the precursor of the alpha pheromone (MFalphal) and deduced from the sequence of this gene that this alpha factor of 13 amino acids was synthesized in the form of a precursor preproprotein of 165 amino acids. The precursor contains an amino-terminal hydrophobic signal sequence of 19 residues followed by a "pro" sequence of 64 amino acids containing 3 glycosylation sites, this sequence itself being followed by the sequence Lys-Arg preceding 4 copies of the alpha factor separated by spacer peptides.

It has been demonstrated that the signal sequence is effectively cleaved in the endoplasmic reticulum by a specific peptidase. The "pro" sequence undergoes an N-glycosylation initiated in the endoplasmic reticulum. The first stage of proteolytic cleavage is performed by the product of the KEX2 gene, that is to say the endoprotease yscF, at the specific signals Lys-Arg or Arg-Arg. This maturation probably takes place in the Golgi apparatus. It was clearly established that *S. cerevisiae* strains which underwent mutations in the KEX2 gene were no longer able to secrete an active form of the killer protein (Leibowitz and Wickner (1976) PNAS USA 2061–2065) or of the alpha pheromone (Julius et al. (1984) Cell 37, 1075–1089) on account of a defective maturation of these proteins.

On the basis of this work of a fundamental nature, the invention proposes amplification of a functional KEX2 gene in a yeast strain productive of a heterologous protein in order to obtain a mature protein.

The invention proposes, in particular, means for increasing the quantity of mature hirudin secreted by a strain of yeast such as *Saccharomyces cerevisiae*, by furthering the process of maturation.

The subject of the invention is thus a yeast strain productive of a heterologous protein in mature form, comprising at least the following expression block:

- a DNA sequence (Str) containing the signals providing for transcription by the yeast of the sequence coding for a precursor of the maturable protein,
- a DNA sequence (Spr) coding for a pre signal peptide and/or a pro peptide,
- a DNA sequence (Scl) coding for a peptide comprising a site for proteolytic cleavage by the product of all or part of the KEX2 gene,
- a DNA sequence coding for the heterologous protein, which, with the Spr sequence, forms the precursor, characterized in that the strain contains one or more copies of all or part of the KEX2 gene leading to an increase in the proteolytic activity of the endoprotease yscF.

As stated above, the invention is most especially well applied to the production of hirudin, in particular of the variant rHV2Lys47.

The KEX2 gene may be obtained, as will be described below, by cloning from a yeast total DNA library. The sequence of the gene is shown in FIG. 2. It has not been repeated in the description in order not to encumber the latter, but it is to be understood that this FIG. 2 forms an integral part of the description.

Different fragments of this gene may be used according to the invention: either the whole of the sequence shown in FIG. 2 from the base 381, which corresponds to the whole of the genomic DNA of the KEX2 if gene; or only the functional sequence of this gene, that is to say that from base 1349 to base 3793 (bounded by the ATG and TGA translation initiation and termination codons) in FIG. 2; or even only a portion of the coding sequence, for example the portion from base 1349 to base 3488 in FIG. 2. The presence of the fragment situated from base 3791 to base 4011 in Figures at the 3' end of the segment of the KEX2 gene improves expression of the gene by playing the part of a terminator and stabilizer of the construction.

It is desirable to delete the fragment from at least base 3491 from base 3489 to base 5790 in FIG. 2, which appears to have a destabilizing role in respect of the messenger RNA.

Amplification of the expression of the gene may be carried out in several ways. In a first variant, one or more copies of all or part of the KEX2 gene are integrated directly in the yeast genome. In a second variant, one or more copies of all or part of the KEX2 gene are inserted into the vector for expression of the heterologous protein, outside the actual expression block. The remainder of the description will concern itself more especially with the second variant.

The product of the KEX2 gene performs proteolytic cleavages specifically. For this reason, the Scl sequences must be chosen from a limited number of possible sequences. The peptides Lys-Arg or Arg-Arg or even Ser-Leu-Asp will preferably be chosen. These Scl sequences can be preceded or otherwise by a "pro" sequence, that is to say they can be associated or otherwise with a complex secretion system. In effect, as long as the site for proteolytic cleavage by the product of the KEX2 gene is present, maturation of the protein can be expected to take place irrespective of the secretion system used: a sequence coding for a pre signal peptide or such a sequence combined with a pro sequence (prepro sequence).

An especially advantageous construction for the production of hirudin is that which combines the prepro sequence of the alpha pheromone of yeast with the Lys-Arg or, where appropriate, Arg-Arg cleavage site. Finally, it is also advantageous to use as an Str sequence a strong promoter in yeast, so as to transcribe a large quantity of mRNA corresponding to the precursor of the maturable protein and use the KEX2 gene with maximum efficiency. As a strong promoter, the promoter of the alpha pheromone of yeast or alternatively the PGK promoter of yeast may be mentioned, for example.

Finally, the expression vectors may possess, after the DNA sequence coding for the mature protein, a terminator sequence of yeast, for example that of the PGK gene.

The expression vectors will, in general, be autonomously replicating plasmids. These plasmids will contain elements providing for their replication, that is to say an origin of replication such as that of the 2 $\mu$ plasmid of yeast. In addition, the plasmid may contain selectable elements such as the URA3 or LEU2 gene, which provides for complementation of ura3 or leu2 yeast mutants. In particular, the URA3 gene from which its promoter has been deleted may advantageously be used.

These plasmids can also contain elements providing for their replication in *E. coli*, when the plasmid must be a shuttle plasmid, for example an origin of replication such as that of pBR322, a marker gene such as $AP^R$ and/or other elements known to those skilled in the art.

Among all the yeast strains which may be envisaged, it will be preferable to use strains of the genus Saccharomyces, in particular the species cerevisiae. When the promoter is that of the MFalphal gene, the yeast will preferably be of the MATalpha mating type. For example, a strain of ura3 or leu2, or the like, genotype, complemented by the plasmid to provide for maintenance of the plasmid in the yeast by a suitable selection pressure, will be used.

Finally, the subject of the invention is a process for preparing a mature heterologous protein by means of yeasts, according to which the strains according to the invention are cultured in a suitable medium and the mature protein secreted into the culture medium is recovered.

More especially, the invention relates to a process for the secretion of hirudin, in particular the variant rHV2Lys47, in mature form from the yeast strains according to the invention.

The examples below will enable other features and advantages of the present invention to be demonstrated. These examples will be illustrated by the following figures:

FIG. 1 shows the sequence of the hirudin variants HV1, HV2 and HV3,

FIG. 2 shows the sequence of the genomic DNA of the KEX2 gene of yeast,

EXAMPLE 1

Cloning of the KEX2 gene

This cloning is carried out by phenotypic complementation of a kex2-1 mutated strain. The mutation of the KEX2 gene is manifested in a MATalpha strain of yeast by the absence of secretion of active alpha pheromone, and in a yeast strain possessing killer RNA (K+) by the absence of secretion of the killer toxin. The strain TGY38.1 is used as receptor strain for cloning of the KEX2 gene. To obtain this strain, the strains 80 (MATa, kex2-1, adeI, ural, [KIL-k] K–R+) [yeast Genetic Stock Center, Berkeley Calif. 94720] and TGY1sp4 (MATalpha, his3, ura3) are first crossed. The diploid obtained, TGY33, is allowed to sporulate. A spore TGY33.1 is then characterized; its genotype is MATa, his3, ura3, kex2-1. A back-cross is performed with TGY1sp4. The diploid obtained, TGY38, is allowed to sporulate. After germination, a segregant TGY38.1 (MATa, ura3, his3, kex2-1) having an improved efficiency of transformation is isolated.

A genomic clone, pTG2809, is obtained from the yeast genomic library (fragments of chromosomal DNA partially digested with Sau3A, which are inserted into the BamHI site of pFL1 [Parent, S. A. et al. Yeast 1 (1985)]. This clone (one (K+) among ten thousand URA+ transformants of the strain TGY38.1) is isolated on the basis of its capacity to abolish the functional defect due to the kex2-1 mutation: secretion of an active killer protein.

By analyzing the DNA sequence (FIG. 2), it is confirmed that the coding sequence of 2442 base pairs is contained in the insert (bounded by the translation initiation and termination codons in FIG. 2). The sequence corresponds to the published sequence of the KEX2 gene [Mizuno K. et al. Biochem. Biophys. Res. Comm. 156 (1988)]. Analysis of the coding sequence of the KEX2 gene reveals information corresponding to a polypeptide of 814 amino acids. The protein would contain a putative signal sequence of approximately 21 amino acids. A hydrophobic portion of 21 amino acids localized close to the C-terminal portion can be detected (position 679–699). The EcoRI fragment, which complements the deficiency due to the kex2-1 mutation, codes for a C-terminally truncated form of the product of the KEX2 gene, representing the portion between the bases numbered 1348 and 3489 (FIG. 2).

EXAMPLE 2

Construction of plasmids pTG3848, pTG3855, pTG3887, pTG3890 and pTG3872

A. Construction of M13TG3841

Figure 3:
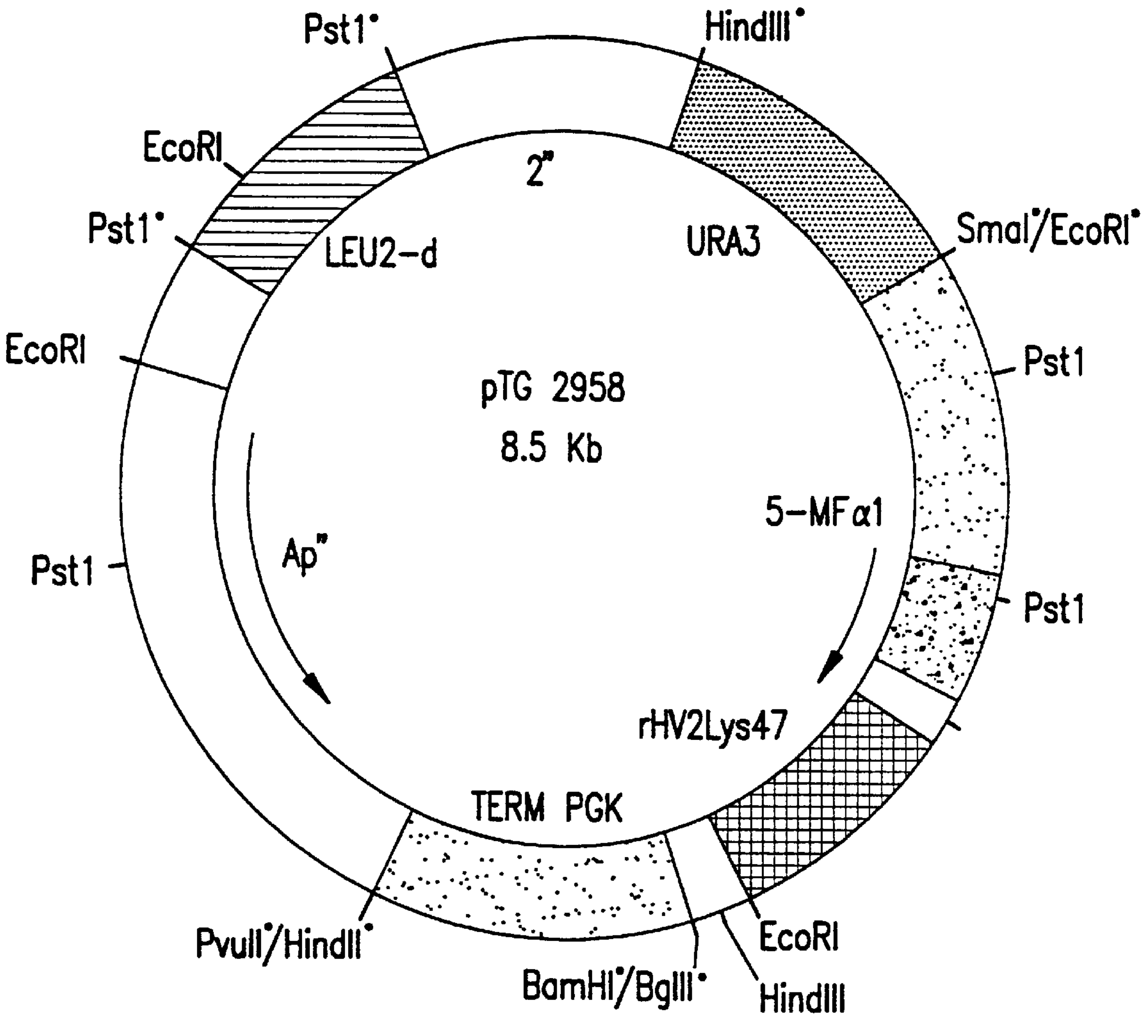
FIG. 3 is a diagrammatic representation of plasmid pTG2958.

Plasmid pTG2958 (FIG. 3) differs little from plasmid pTG1833 described in European Patent Publication EP-A-252,854, carrying the coding sequence for rHV2Asp47. Plasmid pTG2958 does not contain the artificially introduced HindIII restriction site. Plasmid pTG2958 contains:

- a fragment of 547 base pairs corresponding to the 5' region of the Mralphal gene (containing the promoter, the sequence coding for the signal peptide, the "pro" region and a sequence coding for the peptide Lys-Arg), a fragment of 234 base pairs containing the complementary DNA for rHV2Lys47, a fragment of 243 base pairs comprising the PGK terminator of yeast, the PvuII-EcoRI fragment of pBR322 comprising, inter alia, the origin of replication of this plasmid and the gene for resistance to ampicillin (2292 base pairs), the EcoRI-HindIII fragment of the 2 μ plasmid of yeast (B form), containing the LEU2 gene of yeast, in deleted form and inserted into the PstI site, a HindIII-SmaI fragment of the URA3 gene of yeast.

The NcoI-NcoI fragment of the vector pTG2958, which carries the LEU2-d, 2 μ and URA3 sequences, is replaced by the NcoI-NcoI fragment of pTG2800 described in European Patent Publication EP-A-0,268,501, which carries the sequences of the 2 μ plasmid and of the URA3 gene from which its promoter has been deleted (URA3-d), to give pTG2877.

The vector M13TG3839 (FIG. 4) is derived from M13TG103 [Kieny, M. P. et al. Gene 26 (1983)] in which the HindIII-HindIII fragment of pTG2877 is introduced into the same site. A SalI restriction site is introduced into this vector downstream of the translation termination codon of the region coding for rHV2Lys47 by directed mutagenesis using the following oligonucleotide: 5' CAATGAAAAATGGTC-GACTATCAATCATAG to give M13TG3839 SalI. An SphI restriction site is then introduced upstream of the expression cassette, removing the URA3-d sequence by directed mutagenesis using the following oligonucleotide: 5' GACG-GCCAGTGAATTGGCATGCTATTGATAAGATTTAAAG to give M13TG3840.

The vector M13TG131 [Kieny M. P. et al. Gene 26 (1983)] is cleaved with PstI, the ends are made blunt by treatment with the Klenow fragment of DNA polymerase I and the vector is then religated to itself to give M13TG3160. This vector is then cleaved with SmaI and EcoRV and thereafter religated to give M13TG3149.

Figure 4:
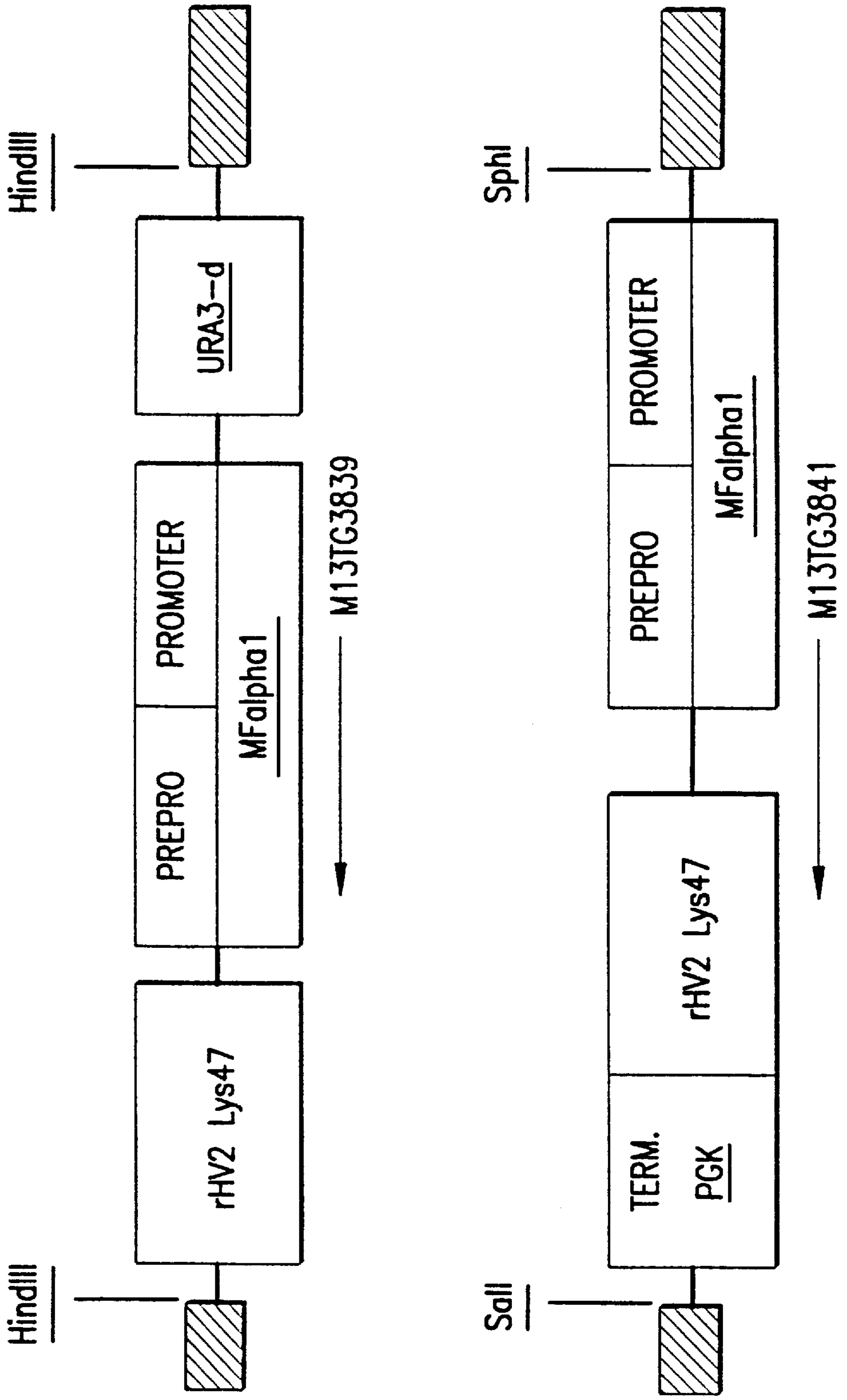
FIG. 4 is a diagrammatic representation of the structure of the vectors M13TG3839 and M13TG3841.

The SphI-SalI fragment of M13TG3840 (described above) carrying the cassette for expression of rHV2Lys47 (without a transcription terminator sequence) is introduced into the SphI-SalI site of M13TG3149 to give M13TG3841 (FIG. 4).

B. Construction of plasmid pTG3848

Plasmid pTG848, described in European Patent Publication EP-A-0,252,854, is digested with BglII and then religated to give pTG2886. The large HindIII-EcoRI fragment of pTG2886 is ligated in the presence of T4 ligase to the 2.1-kb HindIII-EcoRI fragment of plasmid pFL1 [Parent, S. A. et al. Yeast 1 1985] which carries the sequence of the 2 μ plasmid of *S. cerevisiae*, to give plasmid pTG2886 LEU2-d, URA3-d. The 0.9-kb HindIII fragment of plasmid pTG2800 described in the European Patent Publication EP-A-0,258,501, carrying the URA3-d gene, is then inserted into the HindIII site of this plasmid to give pTG2886 URA3-d, delta LEU2-d. The SmaI-BglII fragment of M13TG131 [Kieny et al. Gene 26; 1983] which possesses several restriction sites is then introduced into this plasmid to give pTG3828.

Plasmid pTG3828 is digested with the restriction enzymes SphI-SalI, and the SphI-SalI fragment of the vector M13TG3841 (FIG. 4) is then inserted into this site to give plasmid pTG3848. This plasmid contains:

the sequence of the URA3 gene, from which its promoter has been deleted, the promoter of the MFalphal gene, the prepro sequence of MFalphal, the sequence coding for rHV2Lys47, the transcription terminator of the PGK gene of yeast, a fragment of pBR322 which permits replication and selection in *Escherichia coli,* a fragment of the 2 μ plasmid which possesses the structural elements necessary to replication and to an equal distribution of constituents at mitosis in the yeast.

C. Construction of pTG3855, pTG3887, pTG3890 and pTG3872

Figure 5:
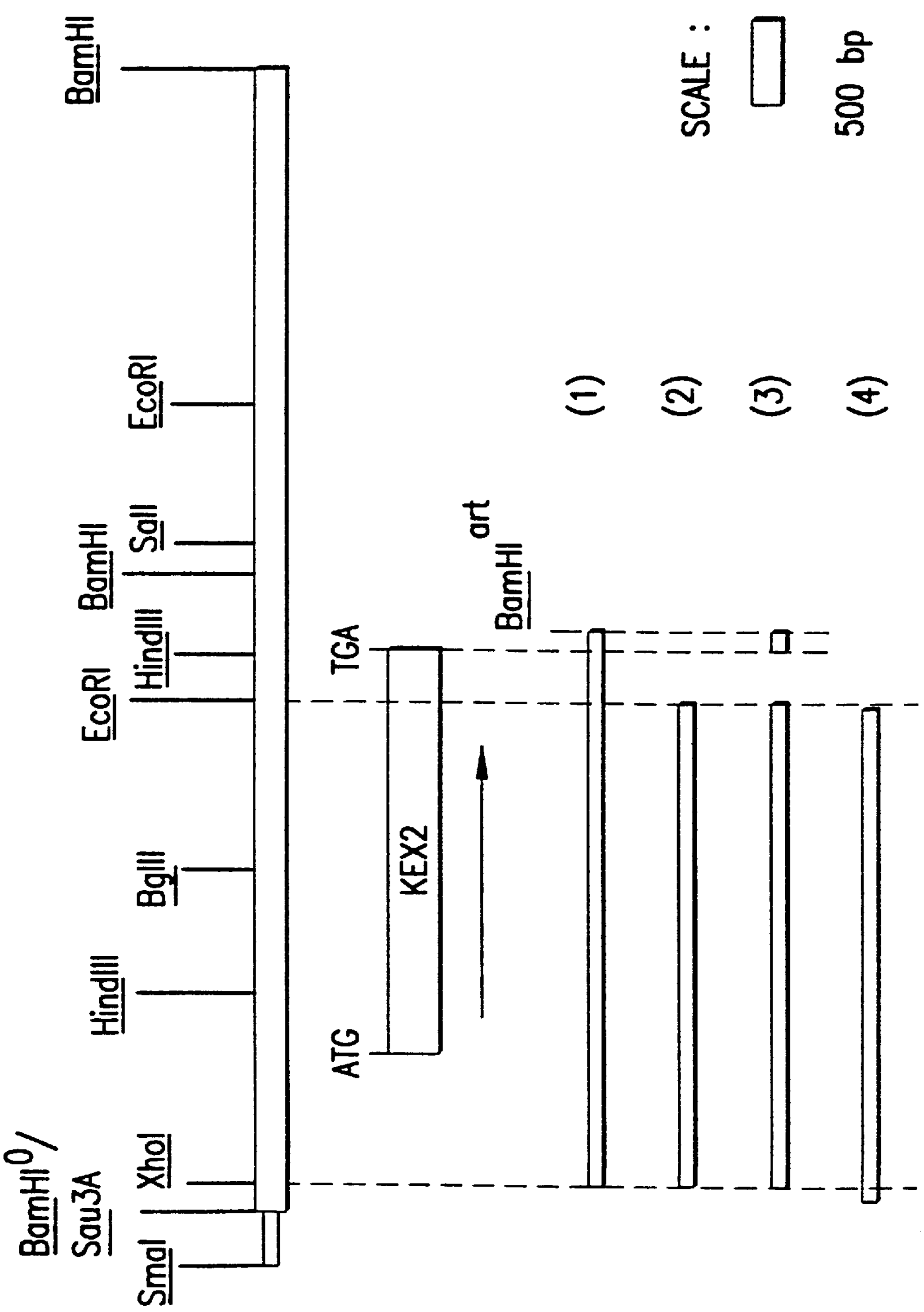
FIG. 5 is a diagrammatic representation of the restriction map of the KEX2 gene fragments used.

These plasmids are derived from pTG3848 opened at the EcoRI site. An artificial BamHI site is created downstream of the stop codon of the KEX2 gene by directed mutagenesis using the following oligonucleotide: 5' TAAAAGGGGAG-GATCCAATTAATGC 3' The XhoI-BamHI fragment (coordinates 538 to 4011, FIG. 2) of pTG2809, comprising all the structural elements of the KEX2 gene (FIG. 5), the ends of which are made blunt with Klenow DNA polymerase, is inserted into the EcoRI site of pTG3848 which has undergone the same treatment, to give plasmid pTG3855. The XhoI-EcoRI fragment (coordinates 538 to 3488, FIG. 2) of pTG2809 (FIG. 5), the ends of which are made blunt with Klenow DNA polymerase, is inserted into the EcoRI site of pTG3848 which has undergone the same treatment, to give plasmid pTG3887 and plasmid pTG3883, depending on the orientation of the fragment. In the case of plasmid pTG3887, the transcription of KEX2 takes place towards the bacterial sequence (pBR322) carried by the plasmid, whereas with plasmid pTG3883, transcription takes place towards the 2 μ sequence of the plasmid. In order to delete the portion of the KEx2 gene between the EcoRI site and the TGA, a directed mutagenesis is carried out using the oligonucleotide of the following sequence: 5' AAGAGCGGAAACGTATGAATGATTC-GATATGTACAGAAAG 3' The artificial XhoI-BamHI fragment (coordinates 538 to 4011, FIG. 2) of pTG2809 thus transformed (FIG. 5), the ends of which are made blunt with Klenow DNA polymerase, is then inserted into the EcoRI site of pTG3848 which has undergone the same treatment, to give plasmid pTG3890. The EcoRI-EcoRI insert of pTG2809 containing the Sau3A-EcoRI fragment of the KEX2 gene (coordinates 381 to 3488, FIG. 2) (FIG. 5) is inserted into the EcoRI site of pTG3848 to give plasmid pTG3872.

EXAMPLE 3

Production of rHV2Lys47 according to the plasmid used

A yeast strain of the species *Saccharomyces cerevisiae* of genotype MATalpha, ura3-251, 373, 328, leu2-3, 112, his3, pep4-3 is transformed with plasmids pTG3848, pTG3872, pTG3855, pTG3887 and pTG3890 by the lithium acetate method [Ito, H. et al. J. Bacteriol. 153; 1983] and the Ura+ prototrophs are selected. They are then cultured in an Erlenmeyer at 30° C. on a selective medium (0.7% of nitrogenous bases for yeasts (Yeast Nitrogen Base), 0.5% of casamino acids and 1% of glucose). After 48 hours of culture, cells and supernatant are separated by centrifugation and the thrombin-inhibitory activity is determined in the supernatant using the colorimetric test (proteolytic activity on a synthetic substrate, chromozyme TH—Boehringer Mannheim). The results of the assays are presented in Table 1; each value corresponds to the mean of two independent experiments. The rHV2Lys47 activity is expressed in ATU/

A600 of the cells ($1-2\times10^7$ cells/ml correspond to 1 A600 nm unit).

TABLE 1

| Plasmid | KEX2 | ATU/A600 |
|---|---|---|
| pTG3848 | — | 8 |
| pTG3872 | [4] | 23 |
| pTG3855 | [1] | 34 |
| pTG3887 | [2] | 34 |
| pTG3890 | [3] | 40 |

The presence of the KEX2 gene on the constructions according to the invention enables the production of rHV2Lys47 in active form to be increased by a factor of five.

EXAMPLE 4

Specific activity of the endoprotease yscF according to the plasmid used

The crude extracts of cultures of yeast strains transformed with plasmids pTG3848, pTG3855, pTG3883 and pTG3890 are recovered according to the procedures described above. The specific activity of the endoprotease yscF is determined by the method described in the publication by Achstetter T. and Wolf D. H. (1985) [EMBO J. 4; p 173–177]. This method is slightly modified, in that Triton is not used, in distinction to these authors. The results of the these assays are presented in Table 2. The specific yscF activity is expressed in mU/mg of protein. The proteins are assayed by a calorimetric method using the kit marketed by BIORAD.

TABLE 2

| Plasmid | KEX2 form | Specific activity |
|---|---|---|
| pTG3848 | — | 2.8 |
| pTG3855 | [1] | 43.7 |
| pTG3883 | [2] | 20.8 |
| pTG3890 | [3] | 74.0 |

The presence of the KEX2 gene in the constructions according to the invention enables the specific activity of the endoprotease yscf produced to be enhanced. It may be concluded from these results that the. fragment between the EcoRI site of KEX2 and the TGA (from at least base 3491 or from base 3489 to base 3790; FIG. 2) appears to play a destabilizing role in respect of the messenger RNA. In contrast, the fragment TGA-BamHI (from the base 3791 to the base 4011; FIG. 2) appears to play the part of a terminator and thereby stabilize the construction. The form of the endoprotease yscf obtained using plasmid pTG3890 hence corresponds to a form whose specific activity is enhanced relative to the reference form.

We claim:

1. A yeast strain that produces a protein heterologous to yeast, wherein the yeast strain comprises at least one copy of a truncated KEX2 gene encoding a protein product having proteolytic activity and an expression cassette comprising in order:

a first DNA fragment comprising a transcription promoter;

a second DNA fragment encoding a signal peptide (pre peptide) or a pre-pro peptide;

a third DNA fragment encoding a site for proteolytic cleavage by the product of said truncated KEX2 gene; and, a fourth DNA fragment encoding said protein heterologous to yeast, and wherein said truncated KEX2 gene is selected from the group consisting of:

(a) a truncated KEX2 gene consisting of bases 381–4011 of the sequence shown in FIG. 2, minus bases 3491–3790;

(b) a truncated KEX2 gene consisting of bases 538–4011 minus bases 3491–3790 of the sequence shown in FIG. 2;

(c) a truncated KEX2 gene consisting of bases 1349–4011 minus bases 3491–3790 of the sequence shown in FIG. 2; and, (d) a truncated KEX2 gene comprising, in order, bases 1349–3490 and 3791–4011 of the sequence shown in FIG. 2, wherein bases 3491–3790 are deleted.

2. The strain according to claim 1, wherein the said protein heterologous to yeast is hirudin.

3. The strain according to claim 2, wherein the hirudin is rHV2Lys47.

4. The strain according to claim 1, wherein at least one copy of the truncated KEX2 gene is integrated directly in the genome of the yeast strain.

5. The strain according to claim 1, wherein the at least one copy of the truncated KEX2 gene and the expression cassette are carried on a vector for expression of the protein heterologous to yeast.

6. The strain according to claim 1, being a strain of *Saccharomyces cerevisiae.*

7. The strain according to claim 5, wherein the vector for expression of the protein heterologous to yeast is a multicopy plasmid.

8. The strain according to claim 5, wherein the vector for expression of the protein heterologous to yeast is an autonomously replicating plasmid.

9. The strain according to claim 1, wherein said third DNA fragment is a sequence coding for a Lys-Arg or Arg-Arg peptide.

10. The strain according to claim 1, wherein said first DNA fragment is a strong promoter in yeast.

11. The strain according to claim 10, wherein the strong promoter is the promoter of an alpha pheromone gene.

12. The strain according to claim 2, wherein said second DNA fragment encodes the prepro peptide of MFalphal.

13. The strain according to claim 12, wherein said second fragment is followed by a sequence coding for a Lys-Arg or Arg-Arg peptide.

14. The strain according to claim 1, wherein said proteolytic activity of the product of the truncated KEX 2 gene is enhanced as compared with the proteolytic activity of the product of the complete KEX2 gene sequence.

* * * * *